US009717569B2

(12) United States Patent
Rodriguez et al.

(10) Patent No.: US 9,717,569 B2
(45) Date of Patent: *Aug. 1, 2017

(54) SURFACE TREATED POLYCRYSTALLINE CERAMIC ORTHODONTIC BRACKET AND METHOD OF MAKING SAME

(75) Inventors: Rodolfo Rodriguez, Mira Loma, CA (US); Albert Ruiz-Vela, Alta Loma, CA (US); Farrokh Farzin-Nia, Inglewood, CA (US); William W. Wood, Pasadena, CA (US)

(73) Assignee: Ormco Corporation, Orange, CA (US)

( * ) Notice: Subject to any disclaimer, the term of this patent is extended or adjusted under 35 U.S.C. 154(b) by 535 days.

This patent is subject to a terminal disclaimer.

(21) Appl. No.: 12/617,507

(22) Filed: Nov. 12, 2009

(65) Prior Publication Data

US 2010/0173256 A1     Jul. 8, 2010

Related U.S. Application Data

(60) Provisional application No. 61/114,565, filed on Nov. 14, 2008.

(51) Int. Cl.
*A61C 3/00* (2006.01)
*A61C 7/14* (2006.01)
*C04B 35/111* (2006.01)

(52) U.S. Cl.
CPC ............ *A61C 7/141* (2013.01); *C04B 35/111* (2013.01); *C04B 2235/6022* (2013.01);
(Continued)

(58) Field of Classification Search
CPC . A61C 7/141; A61C 8/0012; C04B 2235/783; C04B 2235/786; C04B 35/111; C04B 2235/6022; C04B 2235/96
(Continued)

(56) References Cited

U.S. PATENT DOCUMENTS 3,504,438 A    4/1970  Wittman et al.
3,900,542 A *  8/1975  Palmour, III ........... C04B 35/64
                                                      264/40.1
(Continued)

FOREIGN PATENT DOCUMENTS

CA    1326382 C    1/1994
CN    1701764 A   11/2005
(Continued)

OTHER PUBLICATIONS

Eric H. Jordan and Maurice Gell—"Nano Crystalline Ceramic and Ceramic Coatings Made by Conventional and Solution Plasma Spray"—Published on 2005 in Namomaterial Technology for Military Vehicle Structural Applications.*
(Continued)

*Primary Examiner* — Cris L Rodriguez
*Assistant Examiner* — Mirayda A Aponte
(74) *Attorney, Agent, or Firm* — Wood Herron & Evans LLP

(57) ABSTRACT

An orthodontic bracket for coupling an archwire with a tooth. The orthodontic bracket including a ceramic injection molded (CIM) bracket body including an archwire slot that is configured to receive the archwire therein. The CIM bracket body including a polycrystalline ceramic. A coating of alumina or silicon dioxide is in continuous and direct contact with at least the surfaces of the archwire slot. The orthodontic bracket is characterized by unexpectedly high torque strength. The ceramic injection molded (CIM) bracket body may include a polycrystalline ceramic having a grain size distribution characterized by an average grain size in the range of larger than 3.4 μm to about 6 μm such that the orthodontic bracket is also characterized by unexpectedly high fracture toughness. A method of making the orthodontic bracket includes injection molding a bracket (Continued)

using a ceramic powder, sintering the molded bracket, and coating the ceramic injection molded bracket.

54 Claims, 6 Drawing Sheets

(52) U.S. Cl.
CPC .. *C04B 2235/783* (2013.01); *C04B 2235/786* (2013.01); *C04B 2235/96* (2013.01)

(58) Field of Classification Search
USPC ........... 433/2–24; 106/287.11; 501/103–105, 501/127; 585/648; 264/211.11, 500, 299
See application file for complete search history.

(56) References Cited

U.S. PATENT DOCUMENTS

| | | | |
|---|---|---|---|
| 4,050,156 A | 9/1977 | Chasanoff et al. |
| 4,077,126 A | 3/1978 | Pletcher |
| 4,107,844 A | 8/1978 | Kurz |
| 4,180,912 A | 1/1980 | Kesling |
| 4,209,906 A | 7/1980 | Fujita |
| 4,216,583 A | 8/1980 | Reynolds |
| 4,219,617 A | 8/1980 | Wallshein |
| 4,242,085 A | 12/1980 | Wallshein |
| 4,310,306 A | 1/1982 | Wallshein |
| 4,322,206 A | 3/1982 | Reynolds |
| 4,595,598 A | 6/1986 | De Luca et al. |
| 4,626,209 A | 12/1986 | Tsai et al. |
| 4,639,218 A * | 1/1987 | Jones ...................... A61C 7/12 433/8 |
| 4,669,980 A | 6/1987 | Degnan |
| 4,674,978 A | 6/1987 | Acevedo |
| 4,681,538 A | 7/1987 | DeLuca et al. |
| 4,698,017 A | 10/1987 | Hanson |
| 4,780,079 A | 10/1988 | Kato et al. |
| 4,784,606 A | 11/1988 | Jones et al. |
| 4,789,649 A | 12/1988 | Abert et al. |
| 4,799,882 A | 1/1989 | Kesling |
| 4,820,545 A | 4/1989 | Negrych |
| 4,826,430 A | 5/1989 | Chen et al. |
| 4,838,786 A | 6/1989 | Reher et al. |
| 4,842,512 A | 6/1989 | Kesling |
| 4,846,681 A | 7/1989 | Mourany et al. |
| 4,859,179 A | 8/1989 | Kesling |
| 4,877,398 A | 10/1989 | Kesling |
| 4,878,840 A | 11/1989 | Reynolds |
| 4,902,224 A | 2/1990 | Collins et al. |
| 4,915,625 A | 4/1990 | Tsukuma et al. |
| 4,927,360 A | 5/1990 | Pospisil |
| 4,932,865 A | 6/1990 | Collins et al. |
| 4,936,773 A | 6/1990 | Kawaguchi |
| 4,946,387 A | 8/1990 | Adell |
| 4,948,366 A | 8/1990 | Horn et al. |
| 4,954,080 A * | 9/1990 | Kelly ...................... A61C 7/12 433/8 |
| 4,968,459 A | 11/1990 | Sernetz |
| 4,988,293 A | 1/1991 | Collins et al. |
| 5,011,403 A | 4/1991 | Sadoun et al. |
| 5,011,410 A | 4/1991 | Culler et al. |
| 5,022,854 A | 6/1991 | Broughton et al. |
| 5,030,089 A | 7/1991 | Kawaguchi |
| 5,032,081 A | 7/1991 | Farzin-Nia et al. |
| 5,044,945 A | 9/1991 | Peterson |
| 5,061,183 A | 10/1991 | Nicholson |
| 5,064,369 A | 11/1991 | Kawaguchi |
| 5,064,370 A | 11/1991 | Jones |
| 5,066,225 A | 11/1991 | Jones et al. |
| 5,067,897 A | 11/1991 | Tuneberg |
| 5,071,344 A | 12/1991 | Wong et al. |
| 5,074,783 A | 12/1991 | Reher |
| 5,078,596 A | 1/1992 | Carberry et al. |
| 5,094,614 A | 3/1992 | Wildman |
| 5,098,288 A | 3/1992 | Kesling |
| 5,108,285 A | 4/1992 | Tuneberg |
| 5,109,586 A | 5/1992 | Jones et al. |
| 5,110,290 A | 5/1992 | Wong |
| 5,125,832 A | 6/1992 | Kesling |
| 5,126,094 A | 6/1992 | Farzin-Nia et al. |
| 5,147,202 A | 9/1992 | Masuhara et al. |
| 5,154,607 A | 10/1992 | Hanson |
| 5,158,452 A | 10/1992 | Franseen et al. |
| 5,161,969 A | 11/1992 | Pospisil et al. |
| 5,183,403 A | 2/1993 | Masuhara et al. |
| 5,197,873 A | 3/1993 | Wong et al. |
| 5,203,804 A | 4/1993 | Nikutowski et al. |
| 5,219,283 A | 6/1993 | Farzin-Nia et al. |
| 5,219,805 A | 6/1993 | Yoshida et al. |
| 5,231,062 A | 7/1993 | Mathers et al. |
| 5,242,298 A | 9/1993 | Sernetz |
| 5,242,299 A | 9/1993 | Yoshida |
| 5,252,066 A | 10/1993 | Fairhurst |
| 5,254,002 A | 10/1993 | Reher et al. |
| 5,256,062 A | 10/1993 | Griott |
| 5,263,858 A | 11/1993 | Yoshida et al. |
| 5,263,859 A | 11/1993 | Kesling |
| 5,269,680 A | 12/1993 | Kawaguchi |
| 5,302,116 A | 4/1994 | Viazis |
| 5,322,435 A | 6/1994 | Pletcher |
| 5,356,288 A | 10/1994 | Cohen |
| 5,358,402 A | 10/1994 | Reed et al. |
| 5,362,232 A | 11/1994 | Franseen et al. |
| 5,366,372 A | 11/1994 | Hansen et al. |
| 5,374,187 A | 12/1994 | Vashi et al. |
| 5,380,196 A | 1/1995 | Kelly et al. |
| 5,429,500 A | 7/1995 | Damon |
| 5,439,379 A | 8/1995 | Hansen |
| 5,441,408 A | 8/1995 | Moschik |
| 5,466,151 A | 11/1995 | Damon |
| 5,470,228 A | 11/1995 | Franseen et al. |
| 5,474,445 A | 12/1995 | Voudouris |
| 5,474,446 A | 12/1995 | Wildman et al. |
| 5,484,716 A | 1/1996 | Katsumata et al. |
| 5,541,408 A | 7/1996 | Sittler |
| 5,575,644 A | 11/1996 | Tuneburg |
| 5,595,484 A | 1/1997 | Orikasa et al. |
| 5,607,301 A | 3/1997 | Roman |
| 5,613,850 A | 3/1997 | Wildman et al. |
| 5,618,174 A | 4/1997 | Mors |
| 5,618,175 A | 4/1997 | Reher et al. |
| 5,630,715 A | 5/1997 | Voudouris |
| 5,653,588 A | 8/1997 | Moschik |
| 5,656,564 A | 8/1997 | Nakayama et al. |
| 5,681,165 A | 10/1997 | Feldman |
| 5,692,896 A | 12/1997 | Pospisil et al. |
| 5,707,231 A | 1/1998 | Watt et al. |
| 5,716,208 A | 2/1998 | Forman |
| 5,746,594 A | 5/1998 | Jordan et al. |
| RE35,863 E * | 7/1998 | Sachdeva et al. ................ 433/8 |
| 5,782,631 A | 7/1998 | Kesling et al. |
| 5,795,151 A | 8/1998 | Nonami et al. |
| 5,813,852 A | 9/1998 | Kawaguchi |
| 5,816,801 A * | 10/1998 | Farzin-Nia et al. ............. 433/8 |
| 5,854,158 A | 12/1998 | Nawa et al. |
| 5,857,850 A | 1/1999 | Voudouris |
| 5,863,199 A | 1/1999 | Wildman |
| 5,906,486 A | 5/1999 | Hanson |
| 5,908,293 A | 6/1999 | Voudouris |
| 5,911,574 A | 6/1999 | Casey |
| 5,913,680 A | 6/1999 | Voudouris |
| 5,931,667 A | 8/1999 | Papandreas |
| 5,931,668 A | 8/1999 | Birkel |
| 5,944,517 A | 8/1999 | Binder |
| 6,068,473 A | 5/2000 | Birkel |
| 6,071,118 A | 6/2000 | Damon |
| 6,071,119 A | 6/2000 | Christoff et al. |
| 6,071,120 A | 6/2000 | Birkel |
| 6,090,867 A | 7/2000 | Starling, Jr. et al. |
| 6,142,775 A | 11/2000 | Hansen et al. |
| 6,168,428 B1 | 1/2001 | Voudouris |
| 6,193,508 B1 | 2/2001 | Georgakis |
| 6,203,318 B1 | 3/2001 | Birkel |

(56) References Cited

U.S. PATENT DOCUMENTS

| | | |
|---|---|---|
| 6,247,923 B1 | 6/2001 | Vashi |
| 6,257,883 B1 | 7/2001 | Voudouris |
| 6,267,590 B1 | 7/2001 | Barry et al. |
| 6,299,438 B1 | 10/2001 | Sahagian et al. |
| 6,305,932 B1 | 10/2001 | Mottate |
| 6,325,622 B1 | 12/2001 | Kelly et al. |
| 6,368,105 B1 | 4/2002 | Voudouris et al. |
| 6,394,798 B1 | 5/2002 | Huff et al. |
| 6,485,299 B1 | 11/2002 | Wildman |
| 6,540,511 B1 | 4/2003 | Cavaf |
| 6,554,612 B2 | 4/2003 | Georgakis et al. |
| 6,607,383 B2 | 8/2003 | Abels et al. |
| 6,616,445 B2 | 9/2003 | Abels et al. |
| 6,632,088 B2 | 10/2003 | Voudouris |
| 6,644,968 B2 | 11/2003 | Orikasa et al. |
| 6,648,638 B2* | 11/2003 | Castro et al. .................... 433/8 |
| 6,659,766 B2 | 12/2003 | Abels et al. |
| 6,685,468 B1 | 2/2004 | Kesling |
| 6,695,612 B2 | 2/2004 | Abels et al. |
| 6,733,285 B2 | 5/2004 | Puttler et al. |
| 6,733,286 B2 | 5/2004 | Abels et al. |
| 6,746,242 B1 | 6/2004 | Kesling |
| 6,786,720 B1 | 9/2004 | Kesling et al. |
| 6,799,966 B1 | 10/2004 | Horn et al. |
| 6,846,178 B2 | 1/2005 | Freeman, Jr. et al. |
| 6,866,505 B2 | 3/2005 | Senini |
| 6,878,456 B2 | 4/2005 | Castro et al. |
| 6,932,597 B2 | 8/2005 | Abels et al. |
| 6,939,133 B2 | 9/2005 | Voudouris |
| 6,960,079 B2 | 11/2005 | Brennan et al. |
| 6,964,565 B2 | 11/2005 | Abels et al. |
| 6,984,261 B2 | 1/2006 | Cummings et al. |
| 7,014,460 B2 | 3/2006 | Lai et al. |
| 7,022,173 B2 | 4/2006 | Cummings et al. |
| 7,025,591 B1 | 4/2006 | Kesling |
| 7,063,529 B2 | 6/2006 | Abels et al. |
| 7,063,530 B2 | 6/2006 | Abels et al. |
| 7,118,373 B2 | 10/2006 | Abels et al. |
| 7,131,836 B1 | 11/2006 | Kesling |
| 7,140,875 B2 | 11/2006 | Lai et al. |
| 7,140,876 B2 | 11/2006 | Cinader et al. |
| 7,153,130 B2 | 12/2006 | Christoff |
| 7,175,428 B2 | 2/2007 | Nicholson |
| 7,175,833 B1 | 2/2007 | Algar |
| 7,186,115 B2 | 3/2007 | Goldberg et al. |
| 7,192,274 B2 | 3/2007 | Stadtmiller et al. |
| 7,210,927 B2 | 5/2007 | Abels et al. |
| 7,214,057 B2 | 5/2007 | Voudouris |
| 7,217,124 B2 | 5/2007 | Cinader, Jr. et al. |
| 7,217,125 B2 | 5/2007 | Lai et al. |
| 7,234,936 B2 | 6/2007 | Lai et al. |
| 7,247,018 B2 | 7/2007 | Freeman, Jr. et al. |
| 7,247,019 B2 | 7/2007 | Abels et al. |
| 7,255,557 B2 | 8/2007 | Forster |
| 7,264,468 B1 | 9/2007 | Kesling et al. |
| 7,267,545 B2 | 9/2007 | Oda |
| 7,306,457 B2 | 12/2007 | Vigolo |
| 7,323,160 B2 | 1/2008 | Algar et al. |
| 7,326,051 B2 | 2/2008 | Miller |
| 7,331,782 B2 | 2/2008 | Andreiko |
| 7,333,874 B2 | 2/2008 | Taub et al. |
| 7,335,020 B2 | 2/2008 | Castner et al. |
| 7,344,771 B2 | 3/2008 | Kubo et al. |
| 7,361,216 B2 | 4/2008 | Kangas et al. |
| 7,367,800 B2 | 5/2008 | Lai et al. |
| 7,419,375 B2* | 9/2008 | Farzin-Nia ............... A61C 7/20 433/10 |
| 7,655,586 B1* | 2/2010 | Brodkin et al. ............... 501/103 |
| 7,888,279 B2* | 2/2011 | Tsukuma et al. ............ 501/153 |
| 8,251,696 B2* | 8/2012 | Rodriguez et al. ............ 433/10 |
| 2002/0110771 A1 | 8/2002 | Abels et al. |
| 2002/0110773 A1 | 8/2002 | Abels et al. |
| 2002/0110778 A1 | 8/2002 | Abels et al. |
| 2002/0132206 A1 | 9/2002 | Voudouris |
| 2003/0049582 A1 | 3/2003 | Abels et al. |
| 2003/0165790 A1 | 9/2003 | Castro et al. |
| 2004/0043204 A1* | 3/2004 | Nair et al. .................... 428/212 |
| 2004/0063059 A1 | 4/2004 | Meckel |
| 2004/0072117 A1 | 4/2004 | Farzin-Nia et al. |
| 2004/0072119 A1 | 4/2004 | Voudouris |
| 2004/0086824 A1 | 5/2004 | Kesling |
| 2004/0152034 A1 | 8/2004 | Cummings et al. |
| 2004/0229184 A1 | 11/2004 | Senini |
| 2005/0109060 A1 | 5/2005 | Cummings et al. |
| 2005/0136176 A1 | 6/2005 | Rosenflanz et al. |
| 2005/0186525 A1 | 8/2005 | Abels et al. |
| 2005/0239012 A1 | 10/2005 | Bathen et al. |
| 2006/0003282 A1 | 1/2006 | Nicholson |
| 2006/0008761 A1 | 1/2006 | Allred |
| 2006/0051721 A1 | 3/2006 | Carriere Lluch |
| 2006/0057533 A1 | 3/2006 | McGann |
| 2006/0084025 A1 | 4/2006 | Abels et al. |
| 2006/0154195 A1 | 7/2006 | Mather et al. |
| 2006/0163774 A1 | 7/2006 | Abels et al. |
| 2006/0166158 A1 | 7/2006 | Abels et al. |
| 2006/0166159 A1 | 7/2006 | Abels et al. |
| 2006/0172247 A1* | 8/2006 | Abels et al. .................... 433/8 |
| 2006/0177790 A1 | 8/2006 | Farzin-Nia et al. |
| 2006/0199137 A1 | 9/2006 | Abels et al. |
| 2006/0210942 A1 | 9/2006 | Pace et al. |
| 2006/0263736 A1 | 11/2006 | Moon |
| 2006/0263737 A1 | 11/2006 | Oda |
| 2006/0269889 A1 | 11/2006 | Voudouris |
| 2006/0269895 A1 | 11/2006 | Voudouris |
| 2007/0009849 A1 | 1/2007 | Wool |
| 2007/0015104 A1 | 1/2007 | Wiechmann et al. |
| 2007/0072143 A1 | 3/2007 | Sommer |
| 2007/0134609 A1 | 6/2007 | Wyllie et al. |
| 2007/0134610 A1 | 6/2007 | Wyllie et al. |
| 2007/0134611 A1 | 6/2007 | Nicholson |
| 2007/0134612 A1 | 6/2007 | Contencin |
| 2007/0141524 A1 | 6/2007 | Brennan et al. |
| 2007/0160949 A1 | 7/2007 | Voudouris |
| 2007/0166658 A1 | 7/2007 | Voudouris |
| 2007/0178422 A1 | 8/2007 | Voudouris |
| 2007/0190478 A1 | 8/2007 | Goldberg et al. |
| 2007/0207435 A1 | 9/2007 | Devanathan |
| 2007/0207436 A1 | 9/2007 | Tan et al. |
| 2007/0224569 A1 | 9/2007 | Oda |
| 2007/0243497 A1 | 10/2007 | Voudouris |
| 2007/0248926 A1 | 10/2007 | Lai et al. |
| 2007/0248928 A1 | 10/2007 | Damon |
| 2007/0259303 A1 | 11/2007 | Tsukuma et al. |
| 2007/0259304 A1 | 11/2007 | Hagelganz et al. |
| 2007/0269762 A1 | 11/2007 | Kim et al. |
| 2007/0275342 A1 | 11/2007 | Oda |
| 2007/0281269 A1 | 12/2007 | Forster |
| 2008/0038683 A1 | 2/2008 | Von Mandach |
| 2008/0044787 A1 | 2/2008 | Cinader et al. |
| 2008/0081309 A1 | 4/2008 | Wyllie et al. |
| 2008/0096150 A1 | 4/2008 | Cinader |
| 2008/0113311 A1 | 5/2008 | Forster |
| 2009/0004619 A1 | 1/2009 | Oda et al. |
| 2009/0104578 A1 | 4/2009 | Tsukuma et al. |
| 2009/0111067 A1 | 4/2009 | Tsukuma et al. |

FOREIGN PATENT DOCUMENTS

| | | |
|---|---|---|
| CN | 101951855 A | 1/2011 |
| EP | 0430654 A1 | 6/1991 |
| EP | 1070484 A2 | 1/2001 |
| EP | 1787601 A1 | 5/2007 |
| EP | 1836990 | 9/2007 |
| EP | 2055687 | 5/2009 |
| JP | 64-052448 | 2/1989 |
| JP | H08151254 A | 6/1996 |
| JP | 2000-154053 A | 6/2000 |
| JP | 2001029363 A | 2/2001 |
| JP | 2004-57526 | 2/2004 |
| JP | 2005-323694 A | 11/2005 |
| JP | 2005330164 | 12/2005 |
| JP | 2006087915 A | 4/2006 |
| JP | 2006-290688 | 10/2006 |
| JP | 2006326305 A | 12/2006 |

(56) References Cited

FOREIGN PATENT DOCUMENTS

| JP | 2006346188 A | 12/2006 |
|---|---|---|
| JP | 2007-252926 A | 10/2007 |
| MX | 323218 | 8/2014 |
| RU | 1793576 | 9/1995 |
| RU | 2110972 | 5/1998 |
| WO | 89-08085 A1 | 9/1989 |
| WO | 9729712 A1 | 8/1997 |
| WO | 2005084575 | 9/2005 |
| WO | 2005-094715 A1 | 10/2005 |
| WO | 2007-115268 | 10/2007 |
| WO | 2008042678 A1 | 4/2008 |
| WO | 2010019768 A1 | 2/2010 |

OTHER PUBLICATIONS

A. Quade, H. Wulff, H. steffen, T.M. Tun, R. Hippler—"Investigation of the aluminum oxidation in an oxygen plasma excited by microwaves"—Published on 2000 Elsevier Science B.V.*
Fernando Guibeteau, Nitin P. Padture and Brian R. Lawn—"Effect of Grain Size on Hertzian Contact Damage in Alumina"—Published on J. Am. Cerm. Soc., 77 [7] 1825-31 (1994).*
Wei-Chao Gu, Guo-Huan Lv, Huan Chen, Guang-Liang Chen, Wen-Ran Feng, Si-Ze Yang—"Characterisation of ceramic coating producted by plasma electrolytic oxidation of aluminum alloy"—Published on 2006 Elsevier B.V.*
Breviary Technical Ceramics—(http://www.nonmet.mat.ethz.ch/education/courses/Materialwissenschaft_2/brevier.pdf)—Published on Sep. 28, 2006 by the Ceramic Industry Association.*
Breviary Technical Ceramics—(http://www.nonmet.mate.thz.ch/education/courses/Materialwissenschaft_2/brevier.pdf)—Published on Sep. 28, 2006 by the Ceramic Industry Association.*
National Institute of Standards and Technology, Ceramics Web-Book—NIST Property Data Summary of Alumina—http://www.ceramics.nist.gov/srd/summary/ftgal2o3.htm.*
European Patent Office, Invitation to Pay Additional Fees and, Where Applicable, Protest Fee in corresponding PCT Application No. PCT/US2009/053710, Dec. 1, 2009.
European Patent Office, International Search Report and Written Opinion of International Searching Authority in corresponding PCT/US2009/053710, mailed Jan. 19, 2010.
U.S. Patent and Trademark Office, Office Action in U.S. Appl. No. 12/540,627, dated Feb. 10, 2011.
Australian Patent Office, Office Action in Australian Patent Application No. 2009238317, dated Apr. 14, 2011.
Bull, S., "Surface Treatments for Ceramics", http://www.azom.com/details.asp?ArticleID=746.
Bull, S., "Surface Engineering of Ceramics", Materials World, vol. 1, No. 6, pp. 340-342, Jun. 1993.
Russian Patent Office, Office Action in Russian Patent Application No. 2009142016, dated Jan. 25, 2011.
U.S. Patent and Trademark Office, Office Action in U.S. Appl. No. 12/540,638, dated Jul. 15, 2011.
European Patent Office, Office Action in European Patent Application No. 09791489.9, dated Feb. 13, 2012.
Ishitobi, Fabrication of Translucent Al2O3 by High Pressure Sintering, Institute of Scientific and Industrial Research, 1977, vol. 56, No. 6.
Japanese Patent Office, English machine translation of Japanese Patent Publication No. 2006-290688, Application No. 2005-114997, Applicant: Tosoh Corp., entitled "Translucent Ceramic," published Oct. 26, 2006, obtained from Japanese Patent Office website on Nov. 21, 2011.
U.S. Patent and Trademark Office, Notice of Allowance in U.S. Appl. No. 12/540,638, dated Mar. 20, 2012.
European Patent Office, Partial European Search Report in European Patent Application No. EP09252586, dated May 3, 2012.
Japanese Patent Office, Office Action in Japanese Application No. 2009-260208 dated Mar. 13, 2012.
Japanese Patent Office, Office Action in Japanese Patent Application No. 2009-260208 mailed Feb. 19, 2013.
Chinese Patent Office, Office Action in CN200910249078.6 dated Mar. 27, 2013.
Chinese Patent Office, Search Report in CN200910249078.6 dated Mar. 19, 2013.
Japanese Patent Office, Office Action in Japanese Patent Application No. 2013-169444 dated Jul. 7, 2014.
Hwang, C.S., et al., Effect of Sintering Atmosphere on Microstructure and Mechanical Properties of TiO2-Added Zirconia-Toughened Alumina (Part 2), Journal of the Ceramic Society of Japan 104 [1], pp. 1-5 (1996).
Chinese Patent Office, Office Action in Chinese Application No. 200980105523.X, dated Sep. 27, 2013.
European Patent Office, Office Action in European Patent Application No. 09791489.9, dated Jun. 17, 2013.
European Patent Office, Office Action in European Patent Application No. 09791489.9, dated Jan. 23, 2014.
Japanese Patent Office, Office Action in Japanese Patent Application No. 2011-523166, dated Aug. 20, 2013.
Japanese Patent Office, Decision of Rejection in Japanese Patent Application No. 2011-523166, dated Mar. 3, 2014.
Mexican Patent Office, Office Action in Mexican Patent Application No. MX/A/2010/008061, dated May 7, 2013.
Chinese Patent Office, Decision to Grant in Chinese Patent Application No. 200910249078.6, dated Mar. 25, 2014.
Mexican Patent Office, Office Action in Mexican Application No. MX/a/2009/012333 dated Feb. 11, 2015.
Mexican Patent Office, Office Action in Mexican Patent Application No. MX/a/2009/012333, dated Oct. 9, 2015.
Mexican Institute of Industrial Property, Notice of Allowance in Mexican Patent Application No. MX/A/2009/012333, dated Jun. 14, 2016.
Chinese Patent Office, Engilsh Translation of Office Action in Chinese Patent Application No. 201410252656.2, dated May 13, 2016.
Chinese Patent Office, Office Action in Chinese Application No. 201410252656.2 dated May 13, 2016.

* cited by examiner

US 9,717,569 B2

SURFACE TREATED POLYCRYSTALLINE CERAMIC ORTHODONTIC BRACKET AND METHOD OF MAKING SAME

CROSS-REFERENCE TO RELATED APPLICATION

This application claims the benefit of the filing date of U.S. Patent Application Ser. No. 61/114,565, entitled "Surface Treated Polycrystalline Ceramic Orthodontic Bracket and Method of Making Same," filed on Nov. 14, 2008, the disclosure of which is incorporated by reference herein in its entirety.

TECHNICAL FIELD

The invention relates generally to orthodontic brackets and, more particularly, to surface treated polycrystalline ceramic orthodontic brackets.

BACKGROUND

Orthodontic brackets represent a principal component of corrective orthodontic treatments devoted to improving a patient's occlusion. In conventional orthodontic treatments, an orthodontist affixes brackets to the patient's teeth and engages an archwire into a slot of each bracket. The archwire applies corrective pressures that coerce misaligned teeth to move into orthodontically correct positions. Ligatures, such as small elastomeric O-rings or fine metal wires, are employed to retain the archwire within each bracket slot. Alternatively, self-ligating orthodontic brackets have been developed that eliminate the need for ligatures. Instead of using ligatures, self-ligating brackets rely on a movable latch or slide to captivate the archwire within the bracket slot.

Conventional orthodontic brackets are ordinarily formed from stainless steel, which is strong, nonabsorbent, weldable, and relatively easy to form and machine. Patients undergoing orthodontic treatment using metal orthodontic brackets, however, may be embarrassed by the visibility of the metal brackets, which makes treatment obvious even to a casual observer, and, more importantly, is not cosmetically pleasing. To improve the cosmetic appearance, certain orthodontic brackets utilize a bracket body made of a transparent or translucent non-metallic material, such as a polymer resin or a ceramic. The transparent or translucent nature of the bracket may allow the color or shade of the underlying tooth to show through the bracket. For this reason, and as compared to metallic brackets, transparent or translucent brackets are less noticeable and are, therefore, more desirable.

While surpassing metallic brackets aesthetically, ceramic brackets are known to fracture more easily than metal brackets, which are more likely to deform rather than failing catastrophically. Consequently, there is a need for a ceramic bracket that has a greater resistance to tensile and flexural stresses and overcomes other deficiencies of known ceramic brackets.

SUMMARY

To these ends, in one embodiment of the invention, an orthodontic bracket for coupling an archwire with a tooth comprises a ceramic injection molded (CIM) bracket body that is configured to be mounted to the tooth and that includes an archwire slot that is configured to receive the archwire therein. The CIM bracket body comprises a polycrystalline ceramic and a first coating of alumina or silicon dioxide in continuous and direct contact with at least a portion of the CIM bracket body, including the surfaces of the archwire slot.

In another embodiment, an orthodontic bracket for coupling an archwire with a tooth comprises a ceramic injection molded (CIM) bracket body configured to be mounted to the tooth and that includes an archwire slot that is configured to receive the archwire therein. The CIM bracket body comprises a polycrystalline ceramic and a first coating consisting essentially of alumina in contact with at least a portion of the CIM bracket body, including the surfaces of the archwire slot.

In another embodiment, an orthodontic bracket for coupling an archwire with a tooth comprises a ceramic injection molded (CIM) bracket body that is configured to be mounted to the tooth and that includes an archwire slot that is configured to receive the archwire therein. The CIM bracket body comprises a polycrystalline ceramic having a grain size distribution characterized by an average grain size in the range of larger than 3.4 µm to about 6 µm, and a first coating of alumina or silicon dioxide in continuous and direct contact with at least a portion of the CIM bracket body, including the surfaces of the archwire slot.

In another embodiment of the invention, a method of manufacturing an orthodontic bracket for coupling an archwire with a tooth comprises providing a mixture of a ceramic powder and a binder; injecting the mixture into a mold cavity to form a molded bracket body; heating the molded bracket body to substantially remove the binder from the molded bracket body; sintering the molded bracket body to form a ceramic injection molded (CIM) bracket body that is configured to be mounted to the tooth; forming an archwire slot in the CIM bracket body that is configured to receive the archwire therein; and forming a coating of alumina or silicon dioxide in continuous and direct contact with the CIM bracket body over at least a portion of the CIM bracket body, including the archwire slot.

In yet another embodiment, an orthodontic bracket for coupling an archwire with a tooth comprises a ceramic injection molded (CIM) bracket body that is configured to be mounted to the tooth and that includes an archwire slot that is configured to receive the archwire therein. The CIM bracket body comprises a polycrystalline ceramic having a grain size distribution characterized by an average grain size in the range of larger than 3.4 µm to about 6 µm, and a coating of a ceramic in continuous and direct contact with at least a portion of the CIM bracket body, including the surfaces of the archwire slot.

BRIEF DESCRIPTION OF THE DRAWINGS

The accompanying drawings, which are incorporated in and constitute a part of this specification, illustrate embodiments of the invention and, with the general description give above, together with the detailed description given below, serve to explain various aspects of the invention.

DETAILED DESCRIPTION

Figure 1:
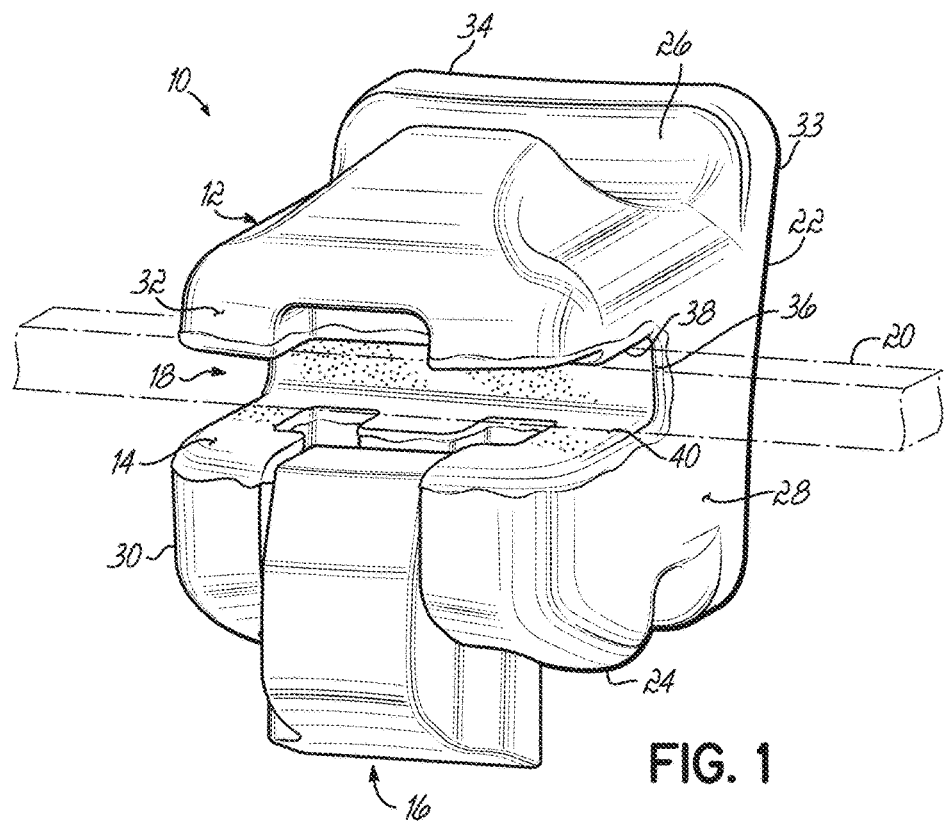
FIG. 1 is a perspective view of an orthodontic bracket in accordance with one embodiment of the invention.

An exemplary orthodontic bracket 10 according to one embodiment of the present invention is depicted in FIG. 1. The orthodontic bracket 10 comprises a ceramic injection molded (CIM) bracket body 12 comprising a polycrystalline ceramic and a coating 14 of alumina ($Al_2O_3$), silicon dioxide ($SiO_2$), zirconia ($ZrO_2$) or another ceramic, such as another oxide, nitride, or boride, covering at least a portion of the CIM bracket body 12. The inventors have discovered that the coating 14 unexpectedly improves the torque strength of the CIM bracket body 12 and counteracts the effects of unique surface defects associated with ceramic injection molding process that are not typically encountered through other manufacturing methods. The coating 14 is described in more detail below.

The orthodontic bracket 10 may also include a movable closure member coupled to the CIM bracket body 12. The movable closure member may include a ligating slide 16 or other mechanical latch coupled with the CIM bracket body 12. The ligating slide 16 may be movable between an open position, as shown in FIG. 1, and a closed position (not shown). While a self-ligating bracket is depicted in FIG. 1, embodiments of the present invention are not limited to self-ligating brackets but are equally applicable to various other types of orthodontic brackets including tiewing-type orthodontic brackets (i.e., those that require ligatures) known in the art of orthodontic treatment.

With reference to FIG. 1, the CIM bracket body 12 includes an archwire slot 18 formed therein and adapted to receive an archwire 20 (shown in phantom line) for applying corrective forces to the teeth when the CIM bracket body 12 is secured to a patient's tooth. When mounted to the labial surface of a tooth carried on the patient's upper jaw, the CIM bracket body 12 has a lingual side 22, an occlusal side 24, a gingival side 26, a mesial side 28, a distal side 30, and a labial side 32. The lingual side 22 of the CIM bracket body 12 is configured to be secured to the tooth in any conventional manner, such as by an appropriate orthodontic cement or adhesive or by a band around an adjacent tooth (not shown). The lingual side 22 may further be provided with a pad 33 that defines a bonding base 34 adapted to be secured to the surface of the tooth. The CIM bracket body 12 includes a base surface 36 and a pair of opposed slot surfaces 38, 40 projecting labially from the base surface 36 that collectively define the archwire slot 18 extending in a mesial-distal direction from mesial side 28 to distal side 30.

Accordingly, with reference to FIG. 1 and in one embodiment of the present invention, the coating 14 covers at least the surfaces 36, 38, and 40 of the archwire slot 18. The coating 14 may be placed, however, on other surfaces, such as any one or more of sides 22, 24, 26, 28, 30 and 32, of the CIM bracket body 12. For example, the coating 14 may be placed on those surfaces that experience contact with the archwire 20, on regions of the CIM bracket body 12 where defects from the injection molding process are known to occur, and/or on surfaces that experience tensile stresses during use or installation. Alternatively, the coating 14 may coat substantially all visible surfaces of the CIM bracket body 12. It will be appreciated that placement of the coating 14 may depend on the process used to form the coating 14.

As provided above, the CIM bracket body 12 is formed by a ceramic injection molding process, as is known in the art, and may be made by ceramic injection molders, such as Tosoh Corporation, Toyko, Japan, and Ceradyne Inc., Costa Mesa, Calif. For example, the CIM bracket body 12 may be made by mixing a ceramic powder, such as alumina powder, with one or more binders to form a paste or thick slurry. The binder (for example, a thermoplastic or thermosetting polymer or a wax) may be formulated to facilitate both flow of the paste during injection and burnout or removal during a subsequent de-binding or presintering operation. The paste may be heated to between 100° C. and 200° C. prior to injection. A high-pressure hydraulic press may be used to inject the heated paste into a mold cavity at pressures up to 100 MPa, though more or less pressure may be used depending on the viscosity of the paste, powder type, and other process factors. The mold cavity at least partially corresponds to the shape of CIM bracket body 12 adjusted to account for shrinkage, if any, during a subsequent sintering operation. In addition, the archwire slot 18 may be fully formed, partially formed, or unformed by the mold cavity.

Following injection molding, the molded CIM bracket body is subject to heating to temperatures known in the art to remove the binders. For example, for alumina, binder removal may occur at temperatures of between 200° C. to 700° C. Following binder removal, the molded CIM bracket body may be presintered by further heating. Presintering high purity alumina (about 99.95 wt. % alumina) may occur at temperatures between 900° C. and 1200° C. Following presintering, the presintered CIM bracket body 12 is sintered. The sintering temperature may be between 1400° C. and 1800° C. depending, for example, on the particle size distribution of the starting powder, other process factors, and the grain size distribution of the polycrystalline ceramic, which is described in more detail below. In other embodiments, the presintered injection molded CIM body may be hot isostatically pressed (HIPed) at pressures of 68 MPa to 207 MPa while at temperatures of between 1300° C. and 1600° C., as is known in the art. It will be appreciated that HIPing may be utilized in addition to the sintering operation. Following sintering and/or HIPing, the CIM bracket body 12 comprises a polycrystalline ceramic characterized by a distribution of grains. In one embodiment, the polycrystalline ceramic comprises alumina having a grain size distribution characterized by an average grain size in a range of larger than 3.4 μm to about 6 μm. As is described below, the polycrystalline ceramic having an average grain size in this range exhibits unexpectedly high fracture toughness.

In one embodiment, following sintering and/or HIPing, the CIM bracket body 12 is annealed, i.e., heated to a temperature and held for a time sufficient to further modify the grain size distribution. Modification of the grains size distribution may occur at temperatures of about 1300° C. or higher. However, higher or lower temperatures than 1300° C. may modify the grain size distribution depending on the time the CIM bracket body 12 is held at the annealing temperature. By way of example, the CIM bracket body 12 may be held at about 1300° C. for about 1 hour. In addition, the bracket body may be heated in a variety of atmospheres including, for example, hydrogen ($H_2$), nitrogen ($N_2$), oxygen ($O_2$), and argon (Ar).

Subsequent to the operations set forth above, in instances where the archwire slot 18 is only partially formed or is not formed by the injection molding process, a grinding operation is required to fully form the archwire slot 18 in the CIM bracket body 12. By way of example and not limitation, the archwire slot 18 may be ground with a 240/320 mesh diamond impregnated wheel.

Figure 2A:
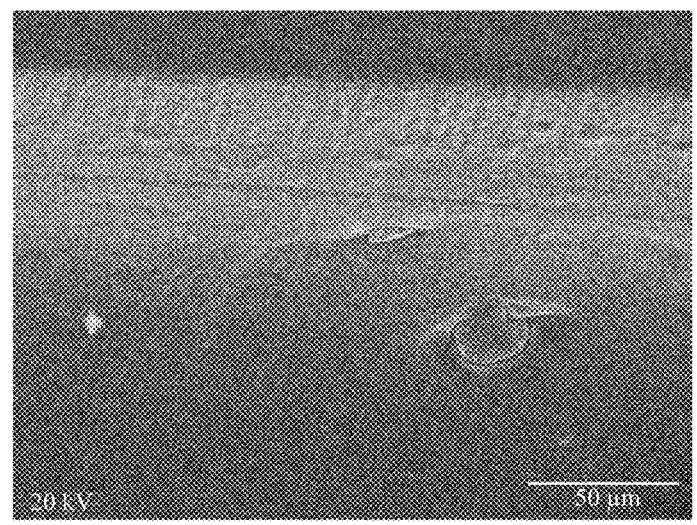
FIG. 2A is an electron micrograph taken at a magnification of 500× of as-formed archwire slot surfaces of a ceramic injection molded (CIM) bracket body depicting defects associated with ceramic injection molding processes.
Figure 2B:
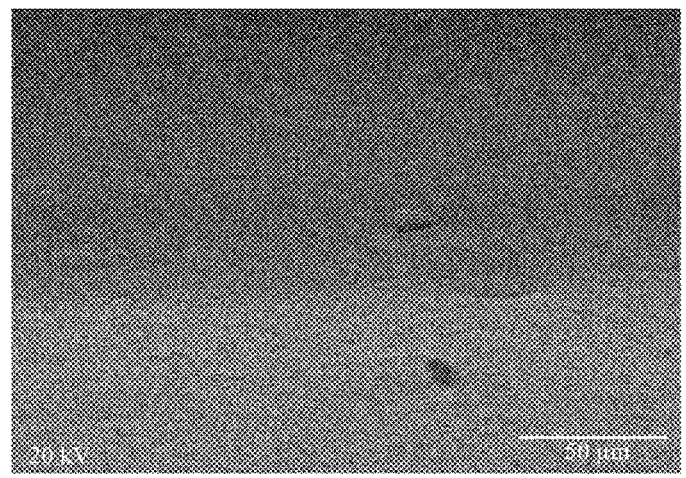
FIG. 2B is an electron micrograph taken at a magnification of 500× of as-formed archwire slot surfaces of a ceramic injection molded (CIM) bracket body depicting defects associated with ceramic injection molding processes.
Figure 2C:
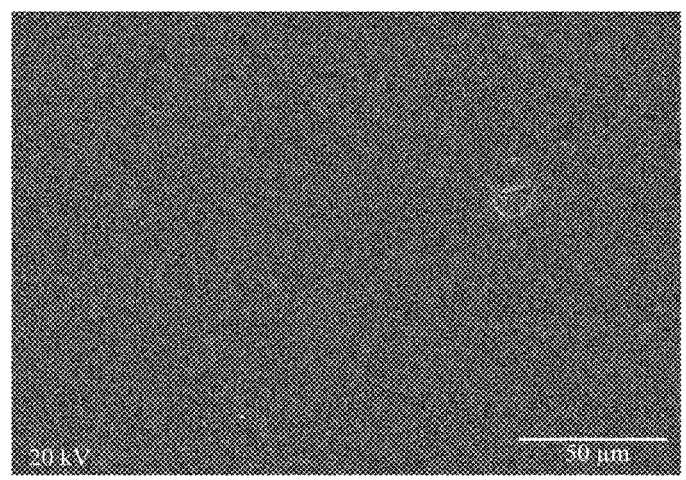
FIG. 2C is an electron micrograph taken at a magnification of 500× of as-formed archwire slot surfaces of a ceramic injection molded (CIM) bracket body depicting defects associated with ceramic injection molding processes.
Figure 2D:
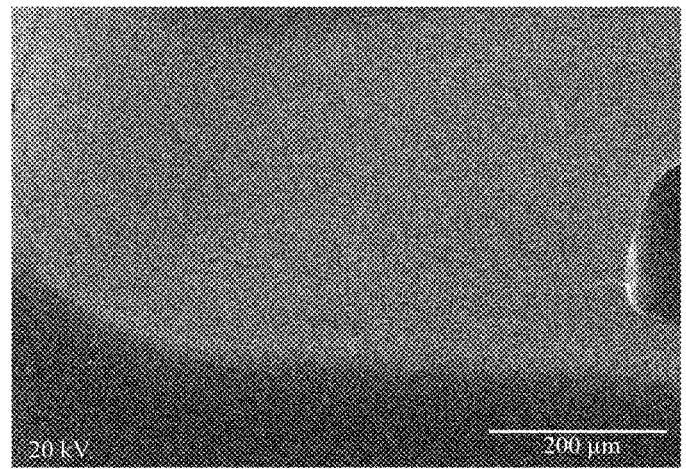
FIG. 2D is an electron micrograph taken at a magnification of 160× of an as-formed archwire slot surface of a CIM bracket body depicting a plurality of defects associated with ceramic injection molding processes.

While ceramic injection molding is an economical process for forming complex shapes, like orthodontic brackets, it causes defects that are unique among ceramic powder forming operations. The defects may be the result of poor mixing, poor pressure or temperature control during injection, mold design, or defects in the mold from operational wear, among others. Examples of surface defects associated with ceramic injection molding are depicted in FIGS. 2A, 2B, 2C, and 2D. The defects include, but are not limited to, localized powder/binder density variations in the CIM bracket body 12 that may cause surface imperfections, such as blisters, in the binder rich areas. Blisters often burst during the binder burnout operation leaving surface defects, as shown in FIG. 2A. By way of additional example, FIG. 2B illustrates the bottom edge of a surface of an archwire slot that has multiple defects. Similarly, FIG. 2C illustrates other defects in the archwire slot, and FIG. 2D, which was taken at lower magnification, illustrates the prevalence of defects in the surfaces of an archwire slot. Other defects include cracks, pores, or both cracks and pores. These defects may be the result of tool wear, sticking between the binder and the mold surface, or blisters to name only a few. In some cases, the powder/binder density variations cause inhomogeneous areas that create residual stresses in the CIM bracket body 12 that are subsequently relieved by microcracking.

The defects are particularly problematic when they occur in or around the archwire slot 18, as shown in FIGS. 2A-2D, or in high tensile stress areas. One skilled in the art will appreciate that to correct misalignment of a tooth, the archwire 20 may apply torque to the CIM bracket body 12 to urge the tooth to its orthodontically correct position. The torque from the archwire 20 forms tensile stresses in the orthodontic bracket 10. The tensile stresses are magnified by the presence of the defects described above. If the tensile stresses, when magnified by any single defect, exceeds the strength of the ceramic bracket, the ceramic bracket fractures. Typically, ceramic brackets fail at stress levels far below what would be predicted based on the ceramic material's theoretical strength.

In an effort to address the problems associated specifically with bracket bodies made by ceramic injection molding, the inventors have discovered that the coating 14 on a portion of the CIM bracket body 12, including the surfaces 36, 38, and 40 of the archwire slot 18, unexpectedly improves the torque strength of the orthodontic bracket 10. In particular, the orthodontic bracket 10 of the present invention is characterized by higher torque strengths than a bracket body of same design without the coating 14. By way of example only, an improvement in torque strength over an as-molded bracket body may be at least approximately 5%; in a further example, the improvement in torque strength may be at least approximately 20%; and, in a further example may be at least approximately 60%. Advantageously, the orthodontic bracket 10 is less likely to fail during handling, installation, or, more importantly, during clinical use. The risk of ingestion or inhalation of the fractured bracket by a patient is therefore less; the patient endures fewer, if any, bracket replacements; and orthodontic treatment proceeds more quickly. In addition, the orthodontic bracket 10 is aesthetically pleasing such that the patient is less self-conscious during treatment.

In one embodiment, the coating 14 is amorphous (an amorphous material lacks long range order in the atomic structure and is not characterized by sharply defined x-ray diffraction peaks). Rather than being amorphous, in another embodiment, the coating 14 comprises nanocrystals, which may measure only two or three unit cells across but are generally less than 100 nm across any one dimension. In one embodiment, the coating 14 comprises crystals such that the microstructure of the coating 14 is finer than the microstructure of the CIM bracket body 12. By way of example, the average size of the crystals in the coating 14 may be less than an average grain size of the CIM bracket body 12. In one embodiment, the coating 14 comprises high purity alumina or silicon dioxide. The crystals or nanocrystals of alumina or silicon dioxide are not contained, even in part, by a matrix of another material, like a glass matrix. Instead, the alumina or silicon dioxide in the form of nanocrystals or in amorphous form is in continuous and direct communication with the CIM bracket body 12. Furthermore, in another embodiment, a coating 14 of alumina is at least about 87.5 wt. % alumina. In a further example, the alumina is at least about 99 wt. % alumina. In yet another example, the alumina is at least about 99.5 wt. % alumina. In one embodiment, the coating 14 consists essentially of alumina. As used herein, "consisting essentially of" means that no other elements are intentionally added to the coating 14. However, impurity content of other elements from the raw materials or the fabrication process may be contemplated.

In one embodiment, the coating 14 may be a thin film of alumina or silicon dioxide formed by vapor depositing the coating 14. The vapor deposited coating may be formed by film deposition techniques known in the art, such as physical vapor deposition (PVD) or chemical vapor deposition (CVD), although other film deposition techniques may be equally suitable.

The coating 14 has a thickness from a few angstroms (e.g., two or three primitive unit cells of alumina or silicon dioxide thick) to about 15 μm or may be other thicknesses that do not detract from the appearance of the CIM bracket body 12 while providing improved torque strength. For example, the coating 14 may be of minimal thickness to produce a continuous coating taking into account the surface roughness of the CIM bracket body 12. Specifically, if the surface roughness of the CIM bracket body 12 is 0.1 μm Ra then the coating thickness may be, on average, about 0.1 μm thick or slightly thicker to form a continuous coating across the surface of the CIM bracket body 12. In a further example, the coating thickness may be between about 1 μm and about 2 μm thick, and, in another example, the coating 14 is about 1.5 μm thick.

Figure 3:
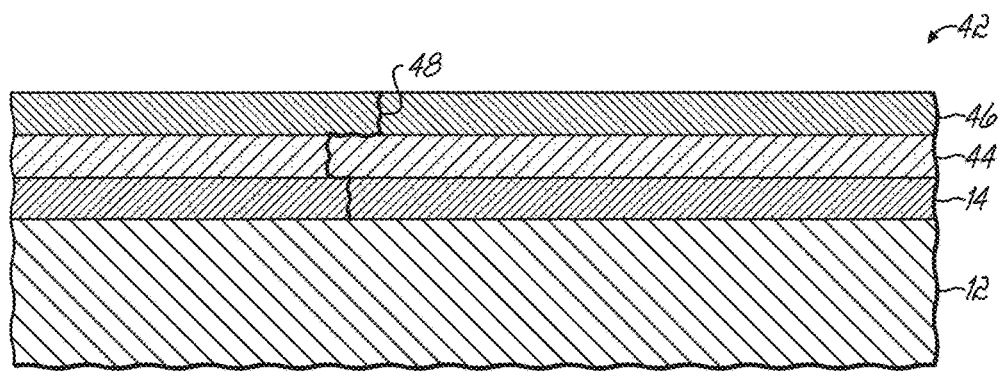
FIG. 3 is a schematic of a multilayered coating on a CIM bracket body according to one embodiment of the invention.

With reference to FIG. 3, in another embodiment, additional coatings are formed on the coating 14 to create a multilayer coating 42 on the CIM bracket body 12. For example, a second coating 44 may be formed over at least a portion of the coating 14 by similar methods used to form the coating 14, described above. In one embodiment shown in FIG. 3, the second coating 44 is in continuous and direct communication with the coating 14. The second coating 44 may be a ceramic, such as alumina, another transparent oxide, nitride, or boride that adheres to the coating 14. Alternatively, the second coating 44 may be a material that is not inherently transparent or translucent but has a thickness that is sufficiently thin to make the multilayer coating 42 comprising the second coating 44 readily transparent or translucent. The second coating 44 may range from a few angstroms thick to about 15 μm thick. In a further example, the second coating 44 may be between about 1 μm and about 2 μm thick, or, in yet another example, about 1.5 μm thick.

As is depicted in FIG. 3, in another embodiment, a third coating 46 may be formed on at least a portion of the second coating 44. The third coating 46 may be the same material as the second coating 44 or the coating 14, or the third coating 46 may be a different ceramic that adheres to the second coating 44 and any portion of the coating 14 and the CIM bracket body 12 that are not covered by the second coating 44. Rather than being substantially the same thickness (as shown in FIG. 3), the individual coatings 14, 44, 46 may be different thicknesses. The multilayer coating 42, overall, is transparent or translucent such that the aesthetic characteristics of the bracket may not be compromised by the multilayer coating 42. While the multilayer coating 42 is depicted as comprising three layers, persons skilled in the art will appreciate that additional layers may be added according to the principles described herein.

Additional layers that form the multilayer coating 42, as shown in FIG. 3, may be achieved, for example, by rotating the CIM bracket body 12 having any previously applied coating out of one coating process and into one or more additional coating process. Alternatively, the multilayer coating 42 may be formed by pulsing or cycling the power source of the coating process such that one or more additional, discrete layers are formed.

In another embodiment of the invention, a portion of the surface of the CIM bracket body 12 is removed prior to coating. By way of example, the portion of the surface removed may include all of the visible surfaces of the CIM bracket body 12 or may include the surfaces within the archwire slot. It is believed that removing the as-formed surface defects from the CIM bracket body 12 prior to coating the CIM bracket body 12 will further enhance the torque strength. An improvement in torque strength over an as-molded bracket body may be at least approximately 5%; in a further example, the improvement in torque strength may be at least approximately 20%; and, in a further example, may be at least approximately 60%. The depth removed is sufficient to remove the defects associated with injection molding and any subsequent processes that are described above. In one embodiment, up to about 15 μm of the surface of the CIM bracket body 12 is removed prior to coating. Removing a portion of the surface may include grinding, etching the surface with a plasma source, etching the surface with an acid (for example, phosphoric, sulfuric, or another acid capable of etching a ceramic material), ion milling the surface, or melting the surface with a laser, or a combination thereof.

In yet another embodiment, the surface of the CIM bracket body 12 may be treated by bombarding the surface with ions. Ion bombardment may occur following removing a portion of the surface of the CIM bracket body 12 or prior to coating an as-molded surface. Ion bombardment may include metal ion bombardment to implant ions into the surface of the CIM bracket body 12 or may include mixed metal ion bombardment followed by noble gas ion bombardment. It is believed that implanting ions into the surface via one or more of the previous processes will impart a compressive residual stress in the surface of the CIM bracket body 12. Torque strength may be observed to increase by at least approximately 5% over an as-molded bracket body; in a further example, the improvement in torque strength may be at least approximately 20%; and, in a further example, may be at least approximately 60% over an as-molded bracket body. Without intending to be bound by theory and with reference to FIG. 1, the inventors believe that the coating 14 of alumina or silicon oxide unexpectedly improves the average torque strength of the CIM bracket body 12 because the coating 14 lowers friction between the archwire 20 and the archwire slot 18 and prevents the archwire 20 from abrading or digging into the CIM bracket body 12 at any single location or along a line within the archwire slot 18. This minimizes the potential for inducing microcracks in the CIM bracket body 12. Further, the coating 14 may prevent surface flaws (for example, those shown in FIGS. 2A-2D) in the surface of the CIM bracket body 12 from opening when subject to tensile loading. The coating 14 may also form compressive stresses in the surface of the CIM bracket body 12. Therefore, tensile stresses generated by torque from the archwire 20 must first overcome the compressive stresses induced in the surface before a net tensile stress is experienced in the surface of the CIM bracket body 12.

In some instances, stresses may be diverted to the coating 14 such that cracks that do form are more likely to form at the surface of the coating 14 rather than in the CIM bracket body 12. Cracks that do initiate at the surface of the coating 14 are thought to travel to the interface between the coating 14 and the CIM bracket body 12 where they are deflected. By deflecting the crack, the crack's length must necessarily increase. By increasing the length of the crack, the tensile stress required to propagate the crack into the CIM bracket body 12 increases, and as a result, the torque strength is improved. With reference to FIG. 3, if multiple coating layers are used, the crack propagation pathway 48 may be further extended, not only by the thickness of each layer but also by the tendency of the crack to propagate along the interface between each layer as shown.

In order to facilitate a more complete understanding of the invention, the following non-limiting examples are provided.

EXAMPLES

Figure 4A:
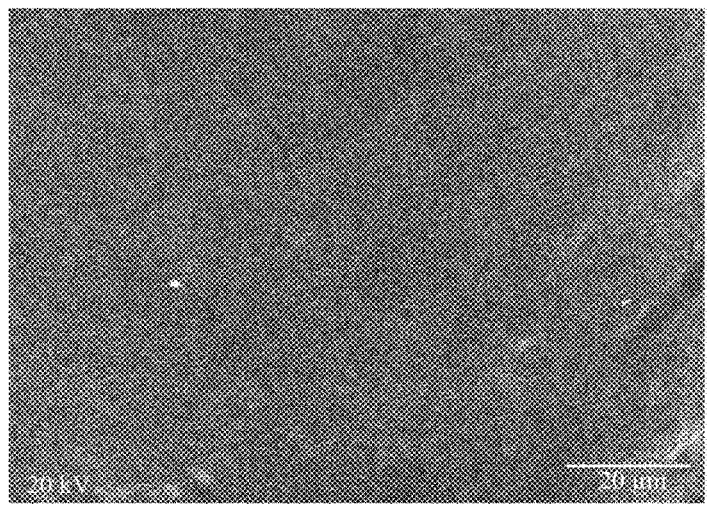
FIG. 4A is an electron micrograph taken at magnification of 1,000× of the surface of a CIM bracket body depicting the microstructure of the surface of the CIM bracket body according to one embodiment of the invention.
Figure 4B:
FIG. 4B is an electron micrograph of a cross section of a CIM bracket body depicting the microstructure within the CIM bracket body according to one embodiment of the invention.

Sample brackets of two different self-ligating bracket designs (Mold A and Mold C, respectively) were purchased from Tosoh Corporation, Tokyo, Japan. Two different polycrystalline alumina compositions were used to mold the Mold A and Mold C brackets. One of the alumina compositions from Tosoh Corporation was identified with the designation PXA-800-A (hereinafter "#1 alumina composition") and the other was identified as PXA-801-A (hereinafter "#2 alumina composition"). The known difference between the two alumina compositions is the binder/powder ratio used during the ceramic injection molding process. The #2 alumina composition had more binder than the #1 alumina composition. In addition to specifying the alumina composition (i.e., #1 alumina composition or #2 alumina composition) from which to form the brackets, the desired average grain size of the microstructure of the brackets was also specified. By way of example only and not limitation, the microstructure of the outer surface of the CIM bracket body received from Tosoh is shown in FIG. 4A and the internal microstructure of the CIM bracket body is shown in FIG. 4B. A portion of the as-received brackets were subject to further surface treatment as described below and were grouped accordingly. The torque strength of each bracket was measured as follows.

Figure 5A:
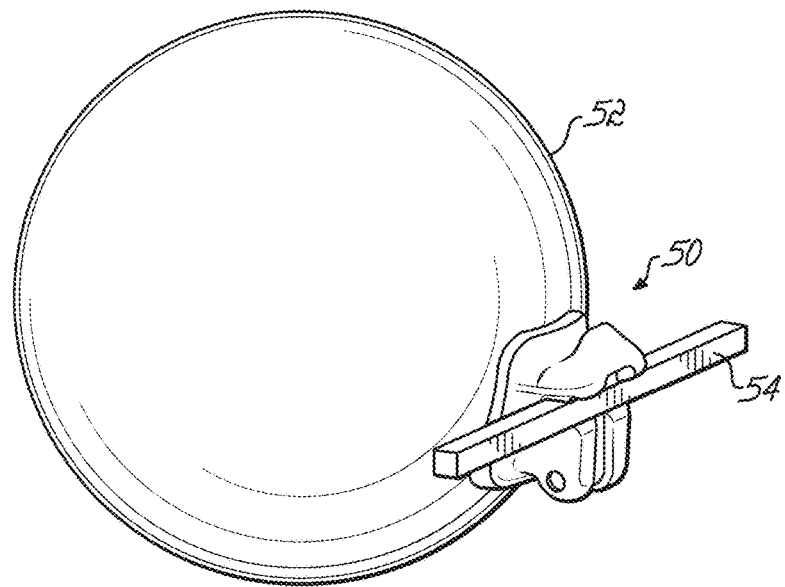
FIG. 5A is a perspective view of a bracket secured to a stainless steel ball bearing according to a procedure for measuring the torque strength of an orthodontic bracket.

With reference to FIG. 5A, each sample bracket 50, following surface treatment, if any, was individually attached to a one-half inch steel ball bearing 52 (the surface of the steel ball was etched prior to attachment) with an adhesive (for example, Loctite® 480, P/N 48040, Henkel Loctite Corporation, Rocky Hill, Conn.). The assembly of the bearing 52 and sample bracket 50, was sprayed with an accelerator (for example, Loctite® 712) to fully cure the adhesive. A rectangular archwire 54 (for example, a 0.018 inch by 0.025 inch stainless steel archwire, Ormco Part No. 254-1825, or a 0.0215 inch by 0.028 inch stainless steel archwire, Ormco Part No. 254-1528) was cut into 1-inch lengths for use with the brackets. Other archwires of different dimensions were also used as indicated below. The self-ligating feature of each bracket was removed. The cut archwire of appropriate size was inserted into the archwire slot of each sample bracket 50. Each archwire 54 was ligated to a bracket with an elastomeric o-ring, namely a Molded Power "O" (0.110 inch) from Ormco Corporation (Ormco Part No. 640-0074) using an elastic positioner (Ormco Part No. 801-0039) taking care to avoid a loose fit between the archwire and archwire slot. In other words, the archwire was selected to fit snuggly, but still seat, within the archwire slot.

Figure 5B:
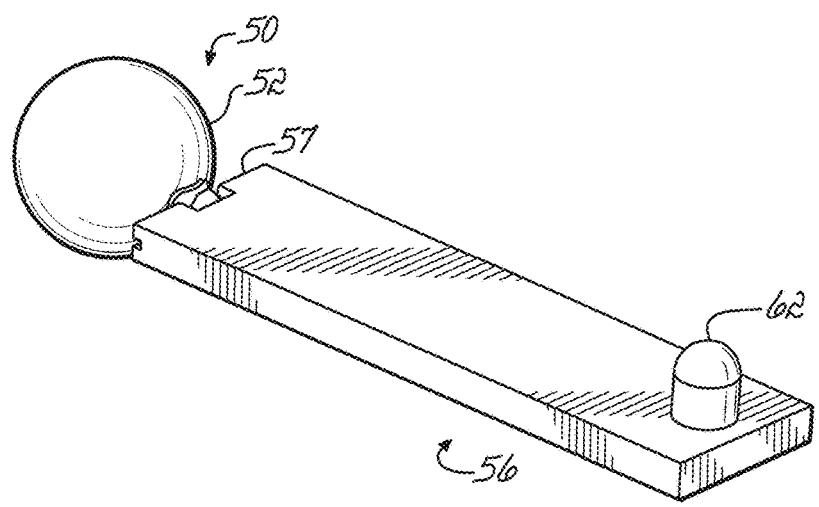
FIG. 5B is a perspective view of the bracket/ball bearing assembly of FIG. 5A assembled with a torque arm according to the procedure for measuring the torque strength of an orthodontic bracket.
Figure 5C:
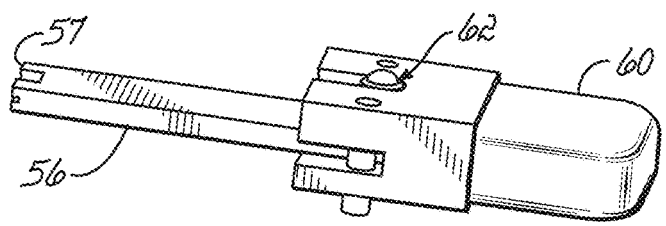
FIG. 5C is a perspective view of the torque arm depicted in FIG. 5B assembled with an arm positioner according to the procedure for measuring the torque strength of an orthodontic bracket.
Figure 5D:
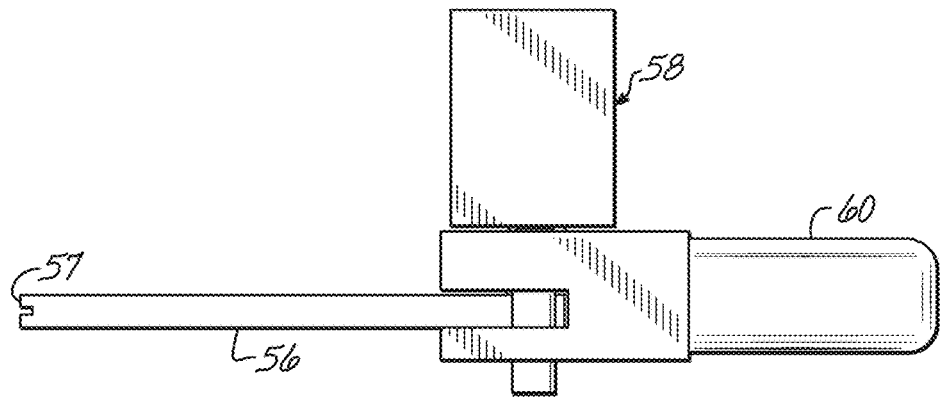
FIG. 5D is a side elevation view of the torque arm of FIG. 5B assembled with the arm positioner of FIG. 5C illustrating their relative position to a compression ram of an Instron 5542.
Figure 5E:
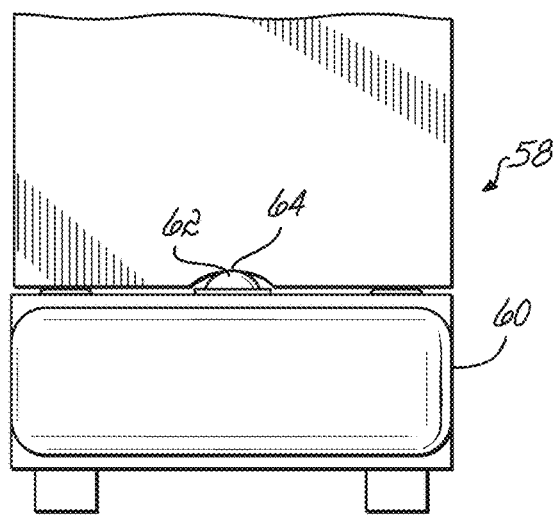
FIG. 5E is a front elevation view of the arm positioner and the compression ram of the Instron 5542 illustrating a torque arm pivot aligned with a recess in the compression ram.

With reference to FIGS. 5A and 5B, the ligated archwire 54 of the sample bracket 50 attached to the ball bearing 52 was engaged with a torque arm 56 for torque strength measurement on an Instron 5542. As shown in FIG. 5A, the gingival side of the bracket 50 was oriented to face in an upward manner to couple with the torque arm 56. The torque arm 56, as shown in FIGS. 5B and 5C, was a steel bar with a forked end 57 having notches in both the vertical direction for clearance around the bracket 50 and in the horizontal direction to allow it to engage the archwire 54 that protrudes from each side of the sample bracket 50. To accommodate the different archwire sizes, a number of torque arms, each having a different horizontal notch size, were used. The horizontal notch in the forked end 57 was sized to accommodate one archwire size (e.g., to accommodate 0.019 inch by 0.025 inch, 0.021 inch by 0.028 inch, or 0.021 inch by 0.025 inch archwires). However, the other dimensions of the torque arm remained the same. Each torque arm 56 was approximately 1.6 inches (4.06 cm) long from the forked end 57 to a torque arm pivot 62 where the load is to be applied. In addition to the length, the portion of the forked end 57 to each side of the vertical notch measured 0.150 inches wide, and the vertical notch for clearance around the bracket 50 measured 0.200 inches wide by 0.150 inches deep. With reference to FIG. 5C, the torque arm 56 was held in a holding slot of an arm positioner 60 which cooperates with the Instron 5542. The ball bearing 52 was clamped in a one-half inch 5C collet (not shown) to hold the torque arm 56 and arm positioner 60 horizontally and perpendicular to the direction of load to be applied by the compression ram 58 of the Instron 5542, as shown in FIG. 5D. With reference to FIG. 5E, the arm positioner 60 was aligned with torque arm pivot 62 in a recess 64 formed in the end of the compression ram 58. The Instron 5542 had a ±100N static load cell and was operated with Bluehill 2 software version 2.13.

The torque strength of each sample was measured by displacing the torque arm/arm positioner (at the torque arm pivot 62) with the compression ram 58 at a rate of 20 mm/min. until the sample bracket broke. The average torque strength for each group was calculated from each bracket's load at failure according to the preceding procedure.

TABLE 1

Mold A brackets

| Group | Average Torque Strength (N) | Number of Brackets Tested | CIM Bracket Body Material | Surface Preparation |
|---|---|---|---|---|
| A | 1.27 ± 0.12 | 5 | alumina[1] | as molded |
| B | 1.30 ± 0.09 | 4 | alumina[1] | etched with a sodium borate solution |
| C | 1.36 ± 0.17 | 6 | alumina[1] | coated with PVD, RF sputtered alumina |
| D | 1.11 ± 0.06 | 5 | alumina[2] | as molded |
| E | 1.39 ± 0.20 | 5 | alumina[2] | 240/320 grit diamond finish |
| F | 1.64 ± 0.12 | 2 | alumina[2] | coated with PVD, RF sputtered alumina |
| G | 1.57 ± 0.09 | 5 | alumina[1] | 3 coats of alumina |

Notes:
[1] polycrystalline alumina from the #1 Alumina composition
[2] polycrystalline alumina from the #2 Alumina composition The sample brackets of Table 1 were all of one self-ligating bracket design designated "Mold A." For all of the brackets, the archwire slot corner radius was 0.005 inch.

The Group A, B, and C brackets had a plain base design and were made of the #1 alumina composition. The mold used to form the brackets of Groups A, B, and C was not polished. The archwires ligated to the Group A, B, and C brackets were made of stainless steel and had a cross section of 0.021 inches by 0.028 inches.

The Groups D, E, and F brackets had an oval base design and were formed of the #2 alumina composition. The portion of the mold that formed the archwire slot of the Groups D, E, and F brackets was polished. The archwires used in the Group E brackets were made of stainless steel and had a cross section of 0.021 inches by 0.028 inches. The archwires used in the Groups D, F, and G brackets were also made of stainless steel but measured 0.019 inches by 0.025 inches.

As noted in Table 1, the brackets of Groups A and D were tested in the as-molded condition, that is, they were not subject to any subsequent surface machining, etching, or coating processes.

The sample brackets of Group B were etched with a supersaturated sodium tetra-borate solution. The sample brackets etched with the supersaturated sodium tetra-borate solution were submersed in the solution for at least 30 seconds to a few minutes. The sample brackets were then heated at about 15° C./minute to a temperature between about 850° C. and about 900° C. and held in that temperature range for between 15 and 30 minutes.

The sample brackets of Group C and F were coated with a PVD radio frequency (RF) sputtered alumina having a thickness of about 1 μm to about 2 μm over the visible surfaces of the bracket, including the archwire slot. X-ray diffraction analysis of some of the coatings was inconclusive as to whether the coatings were amorphous or crystalline. According to the X-ray diffraction data, some of the coatings were amorphous while another exhibited some crystallinity, which indicates that the coatings may be borderline crystalline or may have both amorphous and crystalline regions. It was noted that the x-ray diffraction peaks were relatively broad, like that of an amorphous material, indicating that the coatings may contain very fine crystalline grains.

The sample brackets of Group E were ground with 240/320 grit diamond wheel to remove the as-molded surface of the bracket to a depth sufficient to remove defects associated with the injection molding and sintering processes outlined above.

The sample brackets of Group G were coated with three layers of a PVD RF sputtered alumina each of approximately equal thickness (about 1 μm to about 2 μm each).

As indicated by the data in Table 1, for the #1 alumina composition, the torque strength for the alumina coated sample brackets according to one embodiment of the present invention exhibited an average torque strength of about 1.36N (Group C), which represents a significant improvement in average torque strength, namely an increase of about 7.1% compared to about 1.27N for the as-molded brackets (Group A) and an improvement of about 4.6% compared to about 1.30N for etched brackets of (Group B).

In a further example, for the #2 alumina composition, the sample brackets according to one embodiment of the invention (Group F) had an average torque strength of about 1.64N which was an improvement in torque strength over both the as-mold brackets of Group D, which had an average torque strength of about 1.11N, and the diamond finished brackets of Group E, which had an average torque strength of about 1.39N. Thus, the coated brackets (Group F) according to one embodiment of the present invention were characterized by an unexpected increase in average torque strength of at least approximately 47.7% over as-molded brackets (Group D) and at least approximately 18.0% over diamond finished brackets (Group E).

TABLE 2

Mold C brackets

| Group | Average Torque Strength (N) | Number of Brackets Tested | CIM Bracket Body Material | Surface Preparation |
|---|---|---|---|---|
| H | 1.4 ± 0.10 | 5 | alumina[1] | as molded |
| I | 1.84 ± 0.19 | 5 | alumina[1] | PVD, RF sputtered alumina |
| J | 1.32 ± 0.09 | 4 | alumina[1] | etched with a sodium borate solution |
| K | 1.29 ± 0.08 | 5 | alumina[2] | as molded |
| L | 2.06 ± 0.41 | 5 | alumina[2] | coated with PVD, RF sputtered alumina |
| M | 1.28 ± 0.07 | 5 | alumina[2] | etched with a sodium borate solution |

Notes:
[1]polycrystalline alumina from the #1 Alumina composition
[2]polycrystalline alumina from the #2 Alumina composition With reference now to Table 2, torque strengths of a different self-ligating bracket design (Mold C) were also measured. All of the sample brackets were of a plain base design and the mold used to form each of the brackets was polished prior to making the brackets. The archwire slot corner radius was as molded with a radius of 0.005 inches.

Brackets of Groups H, I, and J were ceramic injection molded of the #1 alumina composition. The archwire used for brackets in Group H, I, and J was made of stainless steel each having a cross section of 0.021 inches by 0.025 inches.

Brackets of Groups K, L, and M were ceramic injection molded of the #2 alumina composition. The archwire used for brackets in Groups K, L, and M was also made of stainless steel but each had a cross section of 0.019 inches by 0.025 inches.

Table 2 provides average torque strength data for the samples measured in the as-molded condition, following etching with a supersaturated sodium borate solution, and following coating with alumina, as described above in conjunction with Table 1.

For the Mold C bracket design made of the #1 alumina composition, the improvement in average torque strength between brackets with an alumina coating according to one embodiment of the present invention (Group I) and the as-molded brackets (Group H) is at least approximately 31.4%. In addition, the alumina coated brackets (Group I) exhibited an improvement in torque strength of at least approximately 39.4% over the etched brackets (Group J).

Similarly, for brackets made of the #2 alumina composition, the alumina coated brackets of Group L according to one embodiment of the present invention have an average torque strength that is at least approximately 59.7% greater than the average torque strength of the as-molded brackets of Group K. The average torque strength of the alumina coated brackets of Group L is at least approximately 60.9% greater than the etched brackets of Group M.

Figure 6A:
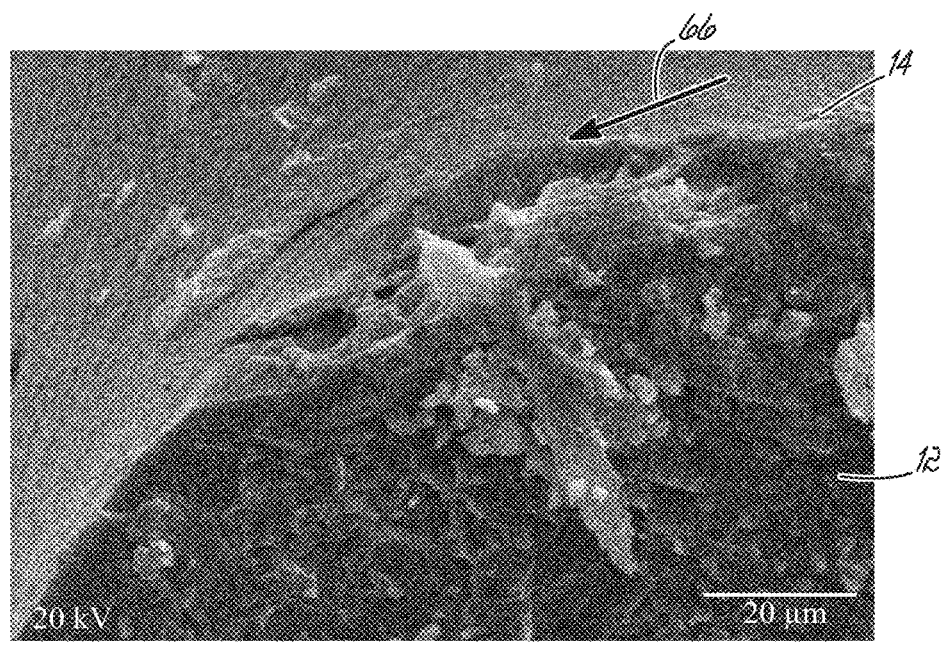
FIG. 6A is an electron micrograph taken at a magnification of 1,000× of exposed fracture surfaces of embodiments of the invention.
Figure 6B:
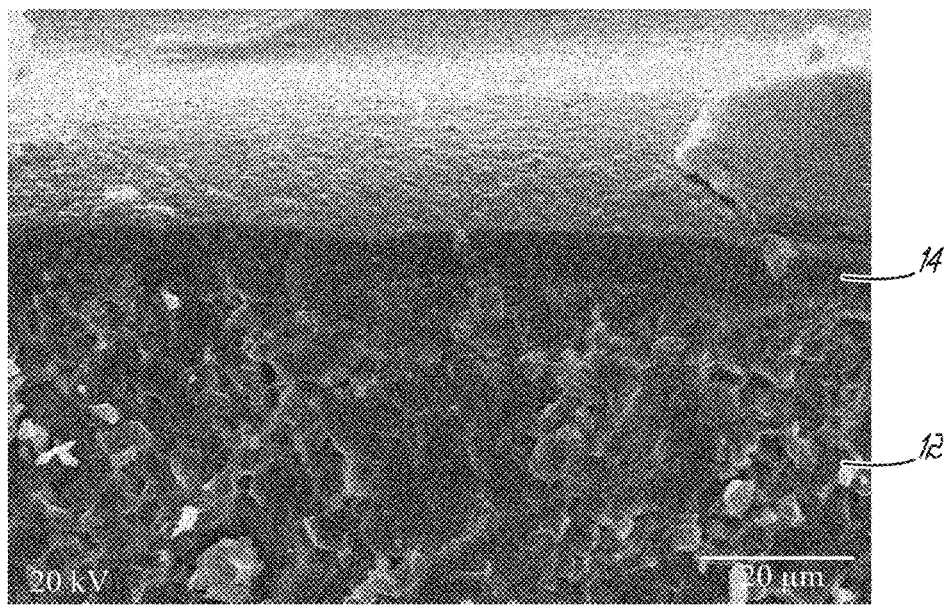
FIG. 6B is an electron micrograph taken at a magnification of 1,000× of exposed fracture surfaces of embodiments of the invention.

As provided above, the improvement in torque strength of the orthodontic bracket 10 over the as-formed brackets, the diamond finished brackets, and the etched brackets is unexpected. It is believed that this unexpected improvement is due in part to deflection of a crack at the coating/CIM bracket body interface, which resulted in an increase in crack length. FIG. 6A depicts a fracture surface of one embodiment of the orthodontic bracket 10. The orthodontic bracket 10 shown in FIG. 6A was a bracket from Group I of Table 2—Mold C brackets. As illustrated by FIG. 6A, crack initiation in the coating 14 appears to have occurred at a location (indicated by an arrow 66 in FIG. 6A) that is offset from the fracture plane through the CIM bracket body 12. Thus, it is believed that the crack was deflected at the coating/CIM bracket body interface such that the crack propagated along the interface to a high stress area at the interface between the coating 14 and the CIM bracket body 12 before proceeding through the CIM bracket body 12. FIG. 6B illustrates another fracture surface of one embodiment of the orthodontic bracket 10. The orthodontic bracket 10 shown in FIG. 6B was a bracket from Group C of Table 1—Mold A brackets. However, in this case, it appears that the crack propagated from the coating 14 to the underlying CIM bracket body 12 in a more direct, planar manner.

As introduced above, in one embodiment of the present invention, the CIM bracket body 12 is made of a polycrystalline ceramic that has a grain size distribution described, in part, by an average grain size in the range of larger than 3.4 μm to about 6 μm. Embodiments of the polycrystalline ceramic having an average grain size in this range are described in U.S. Application No. 61/106,358 titled "Aesthetic Orthodontic Bracket and Method of Making Same" filed on Oct. 17, 2008, the disclosure of which is fully incorporated herein by reference. An average grain size in this range is believed to impart unexpectedly high fracture toughness to the CIM bracket body 12. Thus, embodiments of the orthodontic bracket 10 comprising the CIM bracket body 12 having an average grain size in this range with the coating 14, as set forth above, may have both unexpectedly high fracture toughness and unexpectedly high torque strength.

With regard to fracture toughness, the polycrystalline ceramic exhibits, for example, an average fracture toughness of at least about 3.85 MPa·m$^{1/2}$ and, in a further example, the polycrystalline ceramic having an average grain size between about 4 μm and about 4.3 μm has an average fracture toughness that exceeds about 5.0 MPa·m$^{1/2}$. In other words, the average fracture toughness is believed to peak somewhere in the range above 3.4 μm and at or below about 6 μm, and most likely in the range of about 3.5 μm to about 5.0 μm.

The average grain size as is recited herein may be determined by measuring a plurality of grain lengths on a polished cross section of the polycrystalline ceramic according to the line intercept method. In particular, the average grain size may be calculated from the grain length measurements according to the equation D=1.56 (L), where D is the average grain size and L is the average length of the grains. The average grain size and grain size distribution may also be determined by using commercially available software, such as analySIS software available from Olympus America Inc., Center Valley, Pa., using the grain size module.

The fracture toughness of the polycrystalline ceramic may be determined by at least two methods. One method uses a three-point bend setup to break a bar of the polycrystalline ceramic that contains a flaw or crack of controlled or known size on one surface. In a three-point bend setup, a bar of the material is supported on one side at two locations along the bar's length. Each location is near one of the bar's edges. The distance between the opposing supports is referred to as the support span. A load is applied to the center of the bar on the surface opposite both the supports and the controlled flaw. The load is gradually increased until the bar fractures. This arrangement (i.e., two supports on one side and a load applied between the supports on the opposing side) produces tensile stresses in the surface of the bar containing the flaw of controlled size.

Samples for three-point bend testing are generally in the form of a rectangular bar. For example, a sample of the polycrystalline ceramic for fracture toughness testing may have a thickness of about 1.00±0.1 mm, a width of about 3.00±0.01 mm, and a length of about 12.00±0.01 mm. In addition, a notch having a depth of about 0.050 mm to about 0.100 mm is cut into one surface of the bar at about the bar's midpoint with a diamond abrasive to form the flaw of controlled size. The bar is placed on a support span, which, for example, may measure about 9 mm. A load is applied on the surface opposite the notch until the bar fractures. The fracture toughness may be calculated from the load at fracture according to the equation:

$$K_{IC} = \left(\frac{PS}{wt^{\frac{3}{2}}}\right)\left\{\frac{3}{2}\left(\frac{a}{t}\right)^{\frac{1}{2}} \cdot Y\left(\frac{a}{t}\right)\right\}$$

where $K_{IC}$ is the fracture toughness of the material under a tensile stress that is oriented perpendicular to a crack, P is the load at fracture, S is the support span, w is the bar width, t is the bar thickness, and $$Y\left(\frac{a}{t}\right) = 1.964 - 2.837\left(\frac{a}{t}\right) + 13.711\left(\frac{a}{t}\right)^2 - 23.250\left(\frac{a}{t}\right)^3 + 24.129\left(\frac{a}{t}\right)^4$$

$$a = \frac{a_1 + a_2 + a_3}{3}$$

where a is the average of three crack length measurements, $a_1$, $a_2$, and $a_3$ or is the depth of the crack of known size.

According to another method, fracture toughness can be calculated from Vickers hardness measurements. In this case, the fracture toughness may be calculated according to the following equation, $$K_c = 0.018\left(\frac{E}{HV}\right)^{\frac{1}{2}}\left(\frac{P}{c^{\frac{3}{2}}}\right)$$

where $K_c$ is the fracture toughness, P is the pressing load, E is the modulus, HV is the measured Vickers hardness, and c is one-half of the average of crack length produced by the Vickers hardness indenter. By using this method, rather than testing a bar of the polycrystalline ceramic, fracture toughness may be measured on a bracket body.

In one embodiment, in addition to the average grain size described above, the polycrystalline ceramic is a mixture of both large and small grains. By way of example, the polycrystalline ceramic having a grain size distribution described by an average grain size in the range of greater than 3.4 μm to about 6 μm may further comprise grains larger than 6 μm in size and grains smaller than 3.4 μm in size.

Furthermore, in one embodiment of the orthodontic bracket 10, the CIM bracket body 12 is a polycrystalline ceramic characterized by a grain size distribution that is not a lognormal distribution. By definition, a lognormal distribution is characterized by a random variable whose logarithm is normally distributed about a mean. As an example, the grain size distribution according of the polycrystalline ceramic is multimodal. In particular, the grain size distribution may be a bimodal distribution.

In one embodiment, the grain size distribution is a bimodal distribution having a first peak or mode between a grain size of about 1 μm and about 5 μm and a second peak or mode at a grain size larger than about 5 μm. By way of example, the second peak may be between about 5.5 μm and about 7 μm. However, it will be appreciated that the second peak or additional peaks may occur at grain sizes larger than 7 μm. It will also be appreciated that the bimodal grain size distribution does not describe a duplex microstructure. In one embodiment, the average fracture toughness for a polycrystalline ceramic having an average grain size in the range of larger than 3.4 μm to about 6 μm and at least a bimodal grain size distribution is greater than about 4.0 MPa·m$^{1/2}$.

In addition, the inventors have identified that a grain size distribution characterized by having a particular ratio between grains smaller than about 3 μm and larger grains may further enhance resistance to crack propagation. By way of example, the polycrystalline ceramic may have a grain size distribution having up to about 50% of the total number of grains less than about 3 μm in size. By way of further example, the polycrystalline ceramic may have a grain size distribution having the number of grains less than 3 μm in size of at least 10%. In one embodiment, the number of grains less than 3 μm in size is, for example, between about 10% and about 50% of the total number of grains. In yet another example, the polycrystalline ceramic may be characterized by a grain size distribution having up to about 90% of the total number of grains less than about 10 μm in size. In a further example, the total number of grains less than about 10 μm in size is at least 70%. Therefore, in one embodiment the total number of grains less than about 10 μm in size is between about 70% and about 90% of the grains.

In terms of volume fraction, according to one embodiment, the polycrystalline ceramic is characterized by a grain size distribution in which grains larger than 10 μm in size may occupy up to 50% of the total volume. By way of example, in one embodiment, the grains larger than 10 μm in size may be at least 10%, and, in a further example, the grains larger than 10 μm in size may be from about 10% up to 50% of the total volume. The volume fraction of grains larger than about 10 μm can be calculated by determining the volume of the grains of a particular size range, multiplying that volume by the total number of grains in that size range, and then dividing by the total volume of all the grains.

Without intending to be bound by theory, it is thought that the polycrystalline ceramic having a grain size distribution, as described above, lengthens the crack propagation pathway as compared to polycrystalline ceramics having an average grain size outside this range. The grain size distribution is believed to change the direction of a propagating crack and/or to change the mode of crack propagation. In particular, the presence of grain boundaries may affect the crack's propagation direction and/or the crack's mode of propagation. A change in direction and/or change in mode may consume comparatively more energy than the energy required to propagate a crack along a straight path. The mode of crack propagation in polycrystalline ceramics is either intergranular or transgranular or both. Intergranular crack propagation follows the grain boundaries (that is, between grains) while transgranular crack propagation is through the grains. Accordingly, when a propagating crack encounters a grain boundary or a grain, the crack may be forced to change direction, change its mode of propagation (that is, from transgranular to intergranular or vice versa) or change both direction and mode of propagation. By forcing a change in the direction and/or mode of crack propagation, the length of the crack pathway increases, which consumes more energy, and, accordingly, the fracture toughness may increase.

In accordance with changing the mode of crack propagation described above, in one embodiment, the inventors believe that crack propagation through the polycrystalline ceramic may be mixed mode. That is, if a crack propagates into the polycrystalline ceramic, the polycrystalline ceramic may force the crack to change its mode of propagation one time or many times as it proceeds through the polycrystalline ceramic. The presence of grains less than 10 μm in size may foster intergranular crack propagation. But, a crack confronted by a grain 10 μm in size or larger may be forced to change to the transgranular mode of propagation. The mixed mode of crack propagation may, therefore, further lengthen the propagation pathway and, accordingly, further increase fracture toughness of the polycrystalline ceramic.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details and illustrative examples shown and described. Accordingly, departures may be made from such details without departing from the scope of the general inventive concept.

What is claimed is:

1. An orthodontic bracket for coupling an archwire with a tooth, comprising:
   a ceramic injection molded (CIM) bracket body configured to be mounted to the tooth, including an archwire slot configured to receive the archwire therein, the CIM bracket body comprising a sintered polycrystalline ceramic having a grain size distribution characterized by an average grain size in the range of above 3.4 μm and at or below about 6 μm, wherein the grain size distribution is not characterized as a lognormal distribution; and
   a first coating of alumina or silicon dioxide in continuous and direct contact with at least a portion of the CIM bracket body, including the surfaces of the archwire slot.

2. The orthodontic bracket of claim 1 wherein the average grain size is between about 3.5 μm and about 5 μm.

3. The orthodontic bracket of claim 1 wherein the polycrystalline ceramic has a fracture toughness of at least 4.0 MPa·m$^{1/2}$.

4. The orthodontic bracket of claim 1 wherein the grain size distribution is multimodal.

5. The orthodontic bracket of claim 1 wherein the grain size distribution is bimodal.

6. The orthodontic bracket of claim 5 wherein the bimodal grain size distribution has a first peak in grain size between about 1 μm and about 5.5 μm and a second peak in grain size at a grain size greater than about 5.5 μm.

7. The orthodontic bracket of claim 6 wherein the second peak is at a grain size between about 5.5 μm and about 7 μm.

8. The orthodontic bracket of claim 1 wherein between about 10% and about 50% of the grains are less than about 3 μm in size.

9. The orthodontic bracket of claim 1 wherein between about 70% and about 90% of the grains are less than about 10 μm in size.

10. The orthodontic bracket of claim 1 wherein grains larger than 10 µm in size occupy from about 10% up to about 50% of the volume of the CIM bracket body.

11. The orthodontic bracket of claim 1 further comprising: a ligating slide comprising the polycrystalline ceramic.

12. The orthodontic bracket of claim 1 wherein the first coating comprises a vapor deposited alumina.

13. The orthodontic bracket of claim 1 wherein the first coating is amorphous or nanocrystalline.

14. The orthodontic bracket of claim 1 wherein the first coating comprises a microstructure having an average grain size that is less than an average grain size of the sintered polycrystalline ceramic.

15. The orthodontic bracket of claim 1 wherein there is an interface between the first coating and the portion of the CIM bracket body.

16. An orthodontic bracket for coupling an archwire with a tooth, comprising:
a ceramic injection molded (CIM) bracket body configured to be mounted to the tooth, including an archwire slot configured to receive the archwire therein, the CIM bracket body comprising a sintered polycrystalline ceramic having a grain size distribution characterized by an average grain size in the range of above 3.4 µm and at or below about 6 µm, wherein the grain size distribution is bimodal; and
a first coating of alumina or silicon dioxide in continuous and direct contact with at least a portion of the CIM bracket body, including the surfaces of the archwire slot.

17. The orthodontic bracket of claim 16 wherein the average grain size is between about 3.5 µm and about 5 µm.

18. The orthodontic bracket of claim 16 wherein the polycrystalline ceramic has a fracture toughness of at least 4.0 MPa·m$^{1/2}$.

19. The orthodontic bracket of claim 16 wherein the bimodal grain size distribution has a first peak in grain size between about 1 µm and about 5.5 µm and a second peak in grain size at a grain size greater than about 5.5 µm.

20. The orthodontic bracket of claim 19 wherein the second peak is at a grain size between about 5.5 µm and about 7 µm.

21. The orthodontic bracket of claim 16 wherein between about 10% and about 50% of the grains are less than about 3 µm in size.

22. The orthodontic bracket of claim 16 wherein between about 70% and about 90% of the grains are less than about 10 µm in size.

23. The orthodontic bracket of claim 16 wherein grains larger than 10 µm in size occupy from about 10% up to about 50% of the volume of the CIM bracket body.

24. The orthodontic bracket of claim 16 further comprising:
a ligating slide comprising the polycrystalline ceramic.

25. An orthodontic bracket for coupling an archwire with a tooth, comprising:
a ceramic injection molded (CIM) bracket body configured to be mounted to the tooth, including an archwire slot configured to receive the archwire therein, the CIM bracket body comprising a sintered polycrystalline ceramic having a grain size distribution characterized by an average grain size in the range of above 3.4 µm and at or below about 6 µm, wherein between about 10% and about 50% of the grains are less than about 3 µm in size; and
a first coating of alumina or silicon dioxide in continuous and direct contact with at least a portion of the CIM bracket body, including the surfaces of the archwire slot.

26. The orthodontic bracket of claim 25 wherein the average grain size is between about 3.5 µm and about 5 µm.

27. The orthodontic bracket of claim 25 wherein the polycrystalline ceramic has a fracture toughness of at least 4.0 MPa·m$^{1/2}$.

28. The orthodontic bracket of claim 25 wherein the grain size distribution is multimodal.

29. The orthodontic bracket of claim 25 wherein the grain size distribution is bimodal and has a first peak in grain size between about 1 µm and about 5.5 µm and a second peak in grain size at a grain size greater than about 5.5 µm.

30. The orthodontic bracket of claim 29 wherein the second peak is at a grain size between about 5.5 µm and about 7 µm.

31. The orthodontic bracket of claim 25 wherein between about 70% and about 90% of the grains are less than about 10 µm in size.

32. The orthodontic bracket of claim 25 wherein grains larger than 10 µm in size occupy from about 10% up to about 50% of the volume of the CIM bracket body.

33. The orthodontic bracket of claim 25 further comprising:
a ligating slide comprising the polycrystalline ceramic.

34. An orthodontic bracket for coupling an archwire with a tooth, comprising:
a ceramic injection molded (CIM) bracket body configured to be mounted to the tooth, including an archwire slot configured to receive the archwire therein, the CIM bracket body comprising a sintered polycrystalline ceramic having a grain size distribution characterized by an average grain size in the range of above 3.4 µm and at or below about 6 µm, wherein between about 70% and about 90% of the grains are less than about 10 µm in size; and
a first coating of alumina or silicon dioxide in continuous and direct contact with at least a portion of the CIM bracket body, including the surfaces of the archwire slot.

35. The orthodontic bracket of claim 34 wherein the average grain size is between about 3.5 µm and about 5 µm.

36. The orthodontic bracket of claim 34 wherein the polycrystalline ceramic has a fracture toughness of at least 4.0 MPa·m$^{1/2}$.

37. The orthodontic bracket of claim 34 wherein the grain size distribution is multimodal.

38. The orthodontic bracket of claim 34 wherein the grain size distribution is bimodal and has a first peak in grain size between about 1 µm and about 5.5 µm and a second peak in grain size at a grain size greater than about 5.5 µm.

39. The orthodontic bracket of claim 38 wherein the second peak is at a grain size between about 5.5 µm and about 7 µm.

40. The orthodontic bracket of claim 34 wherein grains larger than 10 µm in size occupy from about 10% up to about 50% of the volume of the CIM bracket body.

41. The orthodontic bracket of claim 34 further comprising:
a ligating slide comprising the polycrystalline ceramic.

42. An orthodontic bracket for coupling an archwire with a tooth, comprising:
a ceramic injection molded (CIM) bracket body configured to be mounted to the tooth, including an archwire slot configured to receive the archwire therein, the CIM bracket body comprising a sintered polycrystalline ceramic having a grain size distribution characterized by an average grain size in the range of above 3.4 µm and at or below about 6 µm, wherein grains larger than 10 µm in size occupy from about 10% up to about 50% of the volume of the CIM bracket body; and a first coating of alumina or silicon dioxide in continuous and direct contact with at least a portion of the CIM bracket body, including the surfaces of the archwire slot.

43. The orthodontic bracket of claim 42 wherein the average grain size is between about 3.5 µm and about 5 µm.

44. The orthodontic bracket of claim 42 wherein the polycrystalline ceramic has a fracture toughness of at least 4.0 MPa·m$^{1/2}$.

45. The orthodontic bracket of claim 42 wherein the grain size distribution is multimodal.

46. The orthodontic bracket of claim 42 wherein the grain size distribution is bimodal and has a first peak in grain size between about 1 µm and about 5.5 µm and a second peak in grain size at a grain size greater than about 5.5 µm.

47. The orthodontic bracket of claim 46 wherein the second peak is at a grain size between about 5.5 µm and about 7 µm.

48. The orthodontic bracket of claim 42 further comprising:

a ligating slide comprising the polycrystalline ceramic.

49. An orthodontic bracket for coupling an archwire with a tooth, comprising:

a ceramic injection molded (CIM) bracket body configured to be mounted to the tooth, including an archwire slot configured to receive the archwire therein, the CIM bracket body comprising a sintered polycrystalline ceramic having a grain size distribution characterized by an average grain size in the range of above 3.4 µm and at or below about 6 µm; and a first coating of alumina or silicon dioxide in continuous and direct contact with at least a portion of the CIM bracket body, including the surfaces of the archwire slot and a ligating slide comprising the sintered polycrystalline ceramic.

50. The orthodontic bracket of claim 49 wherein the average grain size is between about 3.5 µm and about 5 µm.

51. The orthodontic bracket of claim 49 wherein the polycrystalline ceramic has a fracture toughness of at least 4.0 MPa·m$^{1/2}$.

52. The orthodontic bracket of claim 49 wherein the grain size distribution is multimodal.

53. The orthodontic bracket of claim 49 wherein the grain size distribution is bimodal and has a first peak in grain size between about 1 µm and about 5.5 µm and a second peak in grain size at a grain size greater than about 5.5 µm.

54. The orthodontic bracket of claim 53 wherein the second peak is at a grain size between about 5.5 µm and about 7 µm.

* * * * *